United States Patent [19]

Butterfield et al.

[11] Patent Number: 5,716,194
[45] Date of Patent: Feb. 10, 1998

[54] SYSTEM FOR INCREASING FLOW UNIFORMITY

[75] Inventors: Robert D. Butterfield, Poway; Gregory L. Voss, Solana Beach, both of Calif.

[73] Assignee: IVAC Medical Systems, Inc., San Diego, Calif.

[21] Appl. No.: 305,677

[22] Filed: Sep. 12, 1994

[51] Int. Cl.⁶ ............................................. F04B 49/00
[52] U.S. Cl. ............................................. 417/43; 417/53
[58] Field of Search ............................ 417/12, 44.1, 45, 417/43, 53, 279, 290, 293, 300, 326; 318/685, 696; 604/153

[56] References Cited

U.S. PATENT DOCUMENTS

| | | | |
|---|---|---|---|
| 4,346,705 | 8/1982 | Pekkarinen et al. | 128/214 |
| 4,653,987 | 3/1987 | Tsuji et al. | 604/153 |
| 4,657,486 | 4/1987 | Stempfle et al. | 604/153 |
| 4,718,576 | 1/1988 | Tamura et al. | 604/153 |
| 4,731,057 | 3/1988 | Tanaka et al. | 604/153 |
| 4,795,314 | 1/1989 | Prybella et al. | 417/43 |
| 4,909,710 | 3/1990 | Kaplan et al. | 604/153 |
| 4,952,124 | 8/1990 | Ogami | 604/153 |
| 5,074,756 | 12/1991 | Davis | 604/153 |
| 5,078,683 | 1/1992 | Sancoff et al. | 417/474 |
| 5,105,140 | 4/1992 | Matthews et al. | 318/696 |
| 5,165,874 | 11/1992 | Sancoff et al. | 604/153 |
| 5,213,573 | 5/1993 | Sorich et al. | 604/153 |

*Primary Examiner*—Timothy Thorpe
*Assistant Examiner*—Xuan M. Thai
*Attorney, Agent, or Firm*—Fulwider Patton Lee & Utecht, LLP

[57] ABSTRACT

A pumping mechanism moving in movement increments is controlled to space those movement increments in direct proportion to the volume resulting from each movement increment. In a further aspect, movement increments are grouped to result in approximately equal volumes per group. The mechanism moves continuously through the movement increments in each group. Groups are spaced to result in approximately equal flow volumes per group. The number of groups decreases as the flow rate increases. The number of movement increments in each group and the volume of each group increase as the flow rate increases.

26 Claims, 11 Drawing Sheets

FIG. 8

| | 5uL | 10uL | 20uL | 40uL |
|---|---|---|---|---|
| NUMBERS OF STEP GROUPS & TIME PERIODS PER CYCLE (79) → | 32 | 16 | 8 | 4 |
| | 3 | 7 | 13 | 25 |
| | 4 | | | |
| | 3 | 6 | | |
| | 3 | | | |
| | 3 | 6 | 12 | |
| | 3 | | | |
| | 3 | 6 | | |
| | 3 | | | |
| | 3 | 6 | 12 | 24 |
| | 3 | | | |
| | 3 | 6 | | |
| | 3 | | | |
| | 3 | 6 | 12 | |
| | 3 | | | |
| | 3 | 6 | | |
| | 3 | | | |
| | 3 | 6 | 12 | 24 |
| | 3 | | | |
| | 3 | 6 | | |
| | 3 | | | |
| | 3 | 6 | 12 | |
| | 3 | | | |
| | 3 | 6 | | |
| | 3 | | | |
| | 4 | 8 | 20 | 127 |
| | 4 | | | |
| | 5 | 12 | | |
| | 7 | | | |
| | 9 | 103 | 107 | |
| | 94 | | | |
| | 3 | 4 | | |
| | 1 | | | |

(77) TARGET VOLUME

NO. OF STEPS PER STEP GROUP (76)

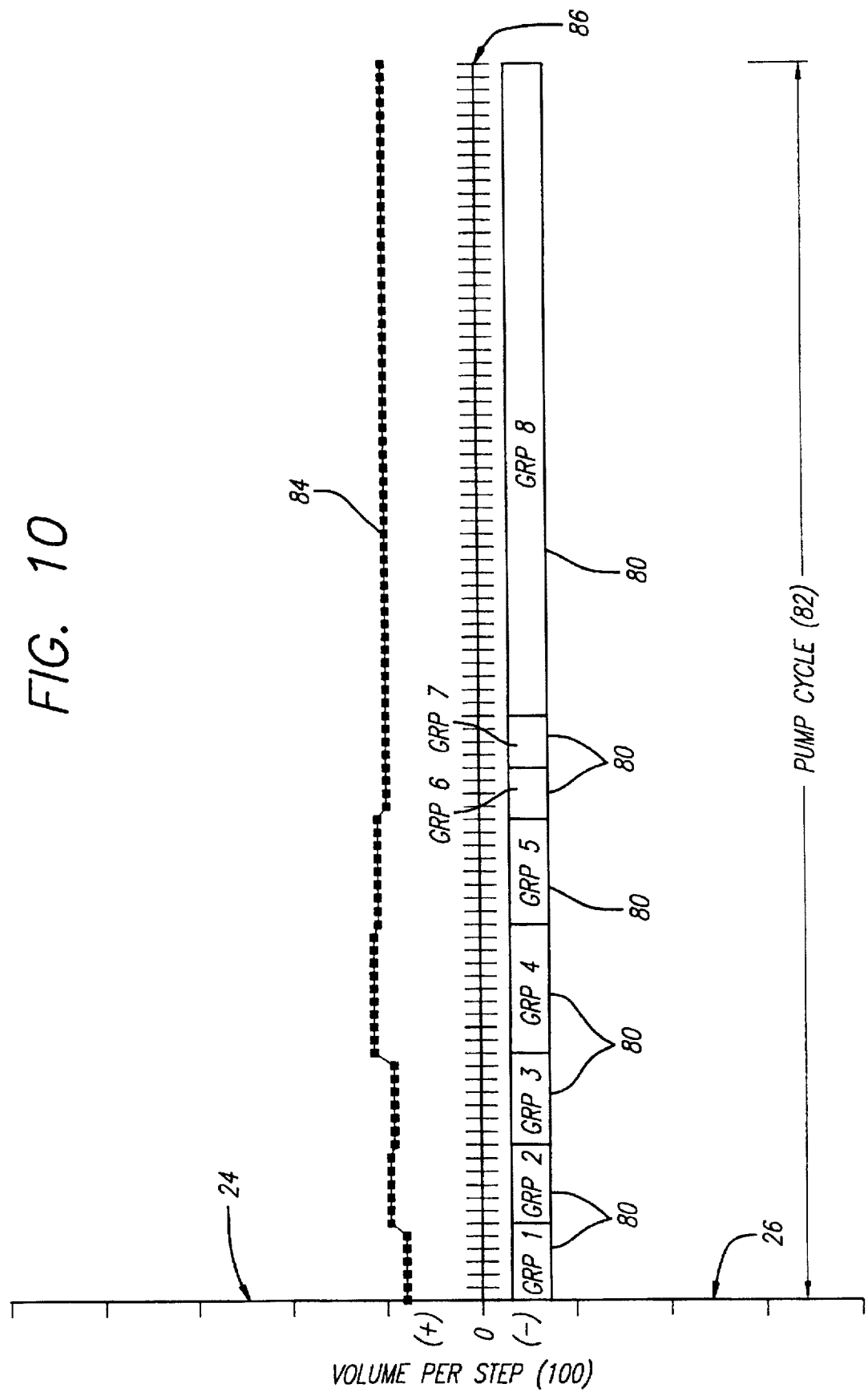

SYSTEM FOR INCREASING FLOW UNIFORMITY

BACKGROUND

The present invention relates generally to controlling the flow of fluids through a conduit and in particular, to controlling a pump acting on a conduit for increasing the uniformity of the fluid flow through the conduit.

In certain systems used for infusing parenteral fluids intravenously to a patient, a pumping mechanism engages a length of tubing or flexible conduit of an administration set to pump the parenteral fluid to the patient at a selected flow rate. A peristaltic pump is one commonly used type of pumping mechanism and employs the sequential occlusion of the administration set conduit to move the fluid through the tubing to the patient.

Linear-type peristaltic pumps include a row of adjacent, reciprocating pumping fingers that are sequentially urged against the fluid administration set conduit to occlude adjacent segments of that tubing in a wave-like action to force fluid through the conduit. The reciprocating, sequential motion of the fingers is accomplished in one arrangement by the use of a cam shaft rotated by a drive motor. Disposed along the length of the cam shaft are a plurality of adjacent cams having generally symmetrical lobe geometries with one cam operating each finger. The cams are disposed along the cam shaft so that adjacent lobes project at different angular positions relative to the cam shaft. The pumping fingers in turn advance and retract sequentially in accordance with the angular positions of the respective cam lobes and rotation of the cam shaft.

The drive motor typically comprises a step motor having a certain number of motor steps per complete rotation of its output shaft; for example, two-hundred steps per 360 degrees of rotation. In general, the step motor output shaft rotates in a sequential, incremental step-by-step manner moving through the motor steps in equal time periods over a complete rotation defining a pump cycle. Typically, a pump cycle is defined as a complete cycle of the pumping mechanism. For example, in the case of a twelve-finger linear peristaltic pump, a pump cycle is complete when all twelve fingers have engaged the fluid conduit and returned to the positions they had at the start of the cycle. In the usual case, the step motor will have also traveled through 360 degrees of rotation thereby causing it to have travelled through all of its steps in that rotation.

Each incremental movement of the motor causes a corresponding incremental movement of the cams and fingers. Because at all times at least one pumping finger is engaging the conduit, each step results in a discrete volume of fluid or "step volume" being pumped through the conduit. A common characteristic of linear peristaltic pumps is that step volumes vary from other step volumes, and at certain points over a pump cycle the step volume may even be negative (the flow reverses). This reverse flow results when the downstream fingers of the linear peristaltic pump are retracted from the conduit and a surge of reverse flow back fills the pumping segment of the conduit from the downstream portion of the conduit due to a pressure difference between the two.

Pump cycle flow patterns for a prior linear peristaltic pump are shown in FIGS. 1 and 2. Both show a pump cycle of two-hundred motor steps. FIG. 1 shows a polar graph of a pump cycle flow pattern for a linear peristaltic pump using a step motor while FIG. 2 shows a linear graph of the same flow pattern.

In FIG. 1, individual motor steps 10 are shown beginning at a reference point "0" and sequentially move in equal angular increments in a clockwise direction over a complete 200-step rotation returning to the reference point "0". The pump cycle flow pattern 12 results. Zero flow is represented by a circle 14, positive flow 16 being represented outside the circle and negative flow 18 being represented inside the circle. A net reverse or negative flow period is pointed out by the arc 20. By referring to the portion of the pattern 12 corresponding to a particular motor step 10, the volume pumped by that step (step volume) can be determined. Step volumes can be measured by means well known to those skilled in the art, such as by gravimetric measurement.

FIG. 2 presents the same data as FIG. 1 except in a linear graph format. Individual motor steps 10 are shown beginning at a reference point "0"defined at the intersection of the X- and Y-axes and each subsequent motor step is represented along the X-axis. The pump cycle flow pattern 12 resulting from the individual step volumes pumped corresponding to each motor step rotated is shown. Zero flow is represented by the X-axis 22, positive flow is represented by the positive Y-axis 24 and negative flow is represented by the negative Y-axis 26. A net reverse or negative flow period 28 is also illustrated. As is apparent from an observation of both FIGS. 1 and 2, different volumes are pumped per motor step during the pump cycle 30.

In one effort to increase the flow uniformity within a peristaltic pump cycle, the design of the pumping mechanism was tailored. For example, tailored, non-symmetrical cam lobes have been developed to accelerate, decelerate or limit the advancement of the pumping fingers as they engage and disengage segments of the tubing. Some of these designs have resulted in increased uniformity of volumes pumped per motor step at a particular design flow rate. However, it has been found that the effectiveness of these designs decreases at flow rates that differ significantly from the design flow rate.

Another effort to increase flow uniformity has been directed primarily at the reverse flow periods 20 and 28 occurring in the pump cycle depicted in FIGS. 1 and 2 respectively. One technique to reduce the effect of the reverse flow is to "speed up" the pump around the reverse flow period of the pumping cycle. During this speed up cycle, the speed of the step motor is increased to move more quickly through the motor steps where reverse flow occurs. The motor thereafter resumes its normal speed over the remaining motor steps in the cycle. This "speed up cycle" has the effect of diluting the reverse flow in that it occurs over a shorter time period.

In FIG. 3, a typical step motor cycle is shown in which the motor continuously moves through the steps, except for the speed-up cycle. The pump is rotating at a steady speed per the selected flow rate and the step motor is moving through its steps in equal periods of time 36. At the point or just before the point where reverse flow would occur, the motor is sped up and faster steps 38 are taken to constitute a speed-up cycle 39, although the motor moves through those steps in equal time periods 38 also. While this technique has proved to be a valuable addition to the art and has increased flow uniformity, the flow pattern continues to appear similar to that shown in FIG. 2 except in the speed-up area 28. As can be seen, the remainder of the pattern has varying flow per step. It is desired to further improve flow uniformity over the complete pump cycle.

Another consideration in pumping mechanisms is the power requirement for the motor to provide the driving force to move the mechanism. Continuously moving a motor for a continuous pumping action can typically require increased power levels. Also, increased power is required for the motor to start from a stop to move a step. This consideration is particularly important in battery powered instruments. Lower power requirements are desired and a system for increasing flow uniformity should not adversely impact power requirements. A further motor consideration is acoustic noise. It has been found that starting and stopping a step motor frequently can result in increased levels of acoustic noise. Likewise a flow uniformity increasing system should not unduly increase the acoustic noise output of the motor and pumping mechanism.

Hence, those skilled in the art have recognized that it is desirable to increase the uniformity of the flow of a pump without the use of specially designed mechanical devices that have limited effectiveness at certain flow rates while at the same time providing a system that may still be operated by battery power and that does not generate objectionable amounts of acoustic noise. The invention fulfills these needs.

SUMMARY OF THE INVENTION

Briefly, and in general terms, the present invention provides a system and method for controlling the flow of fluid in a conduit acted on by a pumping mechanism by controlling the movement of the pumping mechanism to obtain increased flow uniformity. In one aspect, a system for controlling the flow of fluid through a conduit in response to a selected flow rate to provide more uniform flow is provided wherein the system comprises a pumping mechanism acting on the conduit in movement increments with each movement increment resulting in a volume increment pumped through the conduit. The spacing of movement increments is controlled to be directly proportional to the volume increment. A more uniform flow per unit time results.

In a more detailed aspect, the pumping mechanism comprises a step motor coupled to the pumping mechanism to drive the mechanism with each step of the step motor resulting in a respective volume increment moved through the conduit by the pumping mechanism. The processor controls the step motor to space the steps by an amount directly proportional to the volume increments corresponding to the respective steps.

In a further detailed aspect, the pumping mechanism comprises a linear peristaltic mechanism having a plurality of peristaltic fingers, one of which is a downstream finger, all of which are movable into and out of engagement with the conduit, the movement of the fingers being controlled by the step motor. The processor controls the step motor to continuously move through a predetermined number of steps without delay in the event that disengagement of a finger or fingers would result in negative flow in the fluid conduit.

In another aspect of the invention, the processor controls the drive device to move continuously through predetermined numbers of movement increments to form a plurality of groups of movement increments and the processor also controls the drive device to space movement between the groups of movement increments by an amount of time directly proportional to the sum of the volume increments corresponding to the respective group of movement increments. The number of movement increments included in each group of movement increments is selected to result in the sums of the volume increments of each group of movement increments being approximately equal.

In a further detailed aspect, the processor is responsive to a selected flow rate to vary the number of movement increments in each group of movement increments in dependence upon the selected flow rate. In one case, the number of groups of movement increments decreases and the number of number of movement increments in each group increases as the flow rate increases.

The processor controls the pumping mechanism to move each group of movement increments within a predetermined time period and the processor controls the pumping mechanism to continuously move through the movement increments in each group during one portion of the time period and to not move during the remaining portion of the time period. In a detailed aspect, the pumping mechanism continuously moves through the movement increments of each group of movement increments at the beginning of the respective time period and the mechanism does not move for the remainder of the respective time period.

The above results in increased flow uniformity as well as reduced power requirements for supporting the motor operation to provide the groups of steps.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 8 is a table of groups of steps corresponding to different target volumes for a linear peristaltic mechanism driven by a step motor;

FIG. 10 is a linear graph representation of the data shown in FIG. 9; and

DETAILED DESCRIPTION OF THE PREFERRED EMBODIMENTS

Figure 4:
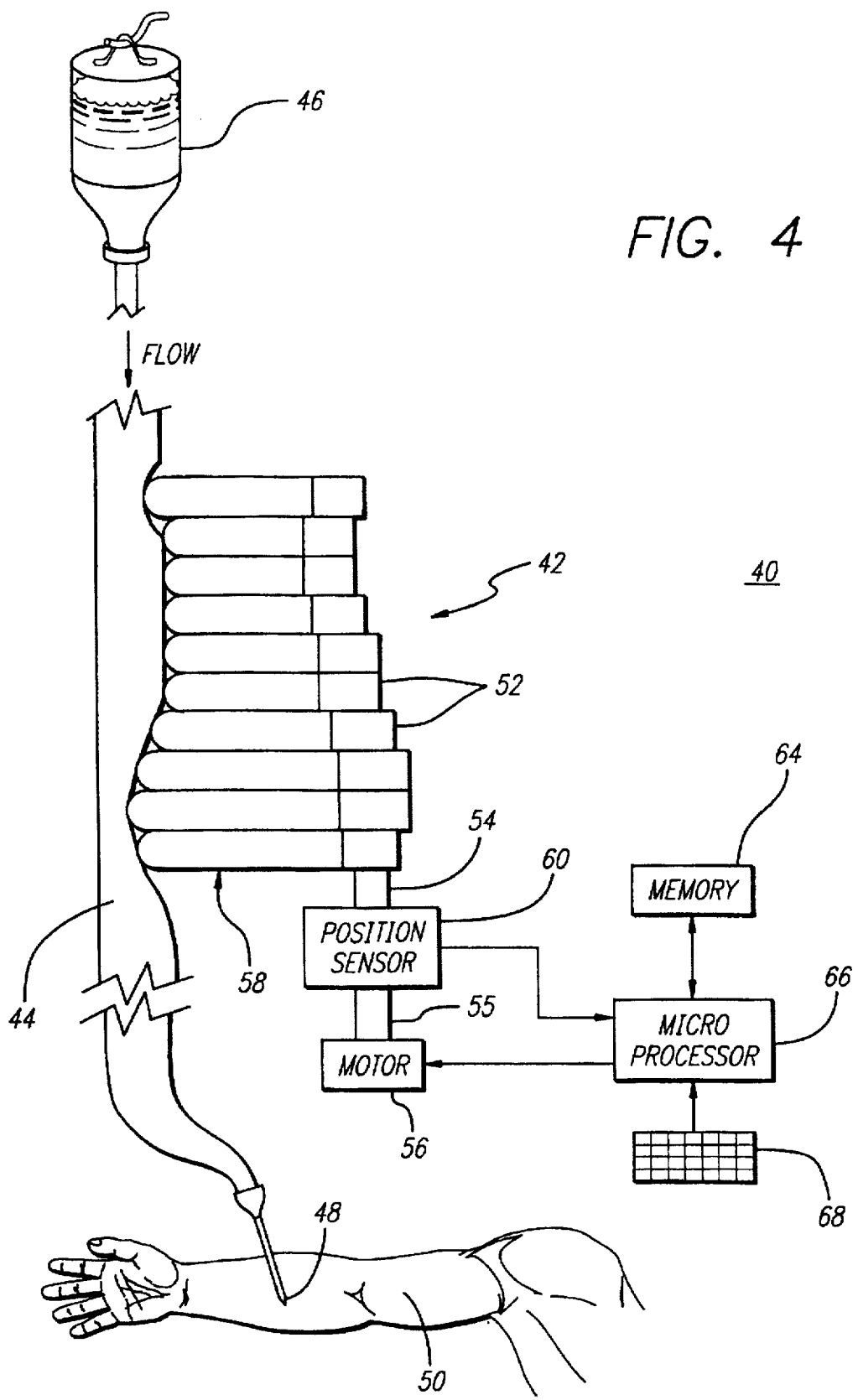
FIG. 4 is a schematic illustration of a linear peristaltic fluid delivery system embodying features of the invention in which a processor controls a drive motor to increase the flow uniformity of parenteral fluid from a fluid reservoir to a patient.

In the following description, like reference numerals will be used to refer to like or corresponding elements in the different figures of the drawings. Referring now to the drawings and particularly to FIG. 4, there is shown a schematic illustration of a parenteral fluid delivery system 40 embodying features of the invention. The fluid delivery system 40 shown comprises a linear peristaltic pump 42 that exerts pressure in a peristaltic wave-like motion against a fluid delivery conduit such as an administrative set tubing 44 to force fluid from a fluid reservoir 46 through a cannula 48 intravenously to a patient 50.

The peristaltic pump 42 includes a plurality of cams 52 mounted to a cam shaft 54, the cam shaft being coupled to the output shaft 55 of a drive motor 56. Although numeral 52 only points to two cams in the figure, it is meant to indicate all cams. In this case, the motor comprises a step motor 56 that travels through a plurality of steps in each complete rotation of its drive member. The cams 52 are coupled to respective pumping FIGS. 58 for accomplishing the act of compressing the tubing 44 in a wave-like motion. The fingers 58 sequentially occlude adjacent portions of the tubing to establish the wave-like peristaltic motion to drive fluid through the tubing to the patient 50 in response to the rotation of the cam shaft 54 by the motor 56. A rotation position sensor 60 is connected to the cam shaft 54 so that the rotational position of the cam shaft can be determined. Although shown mounted on the proximal end of the camshaft, it may be mounted on the distal end instead, or in other positions.

Figure 1:
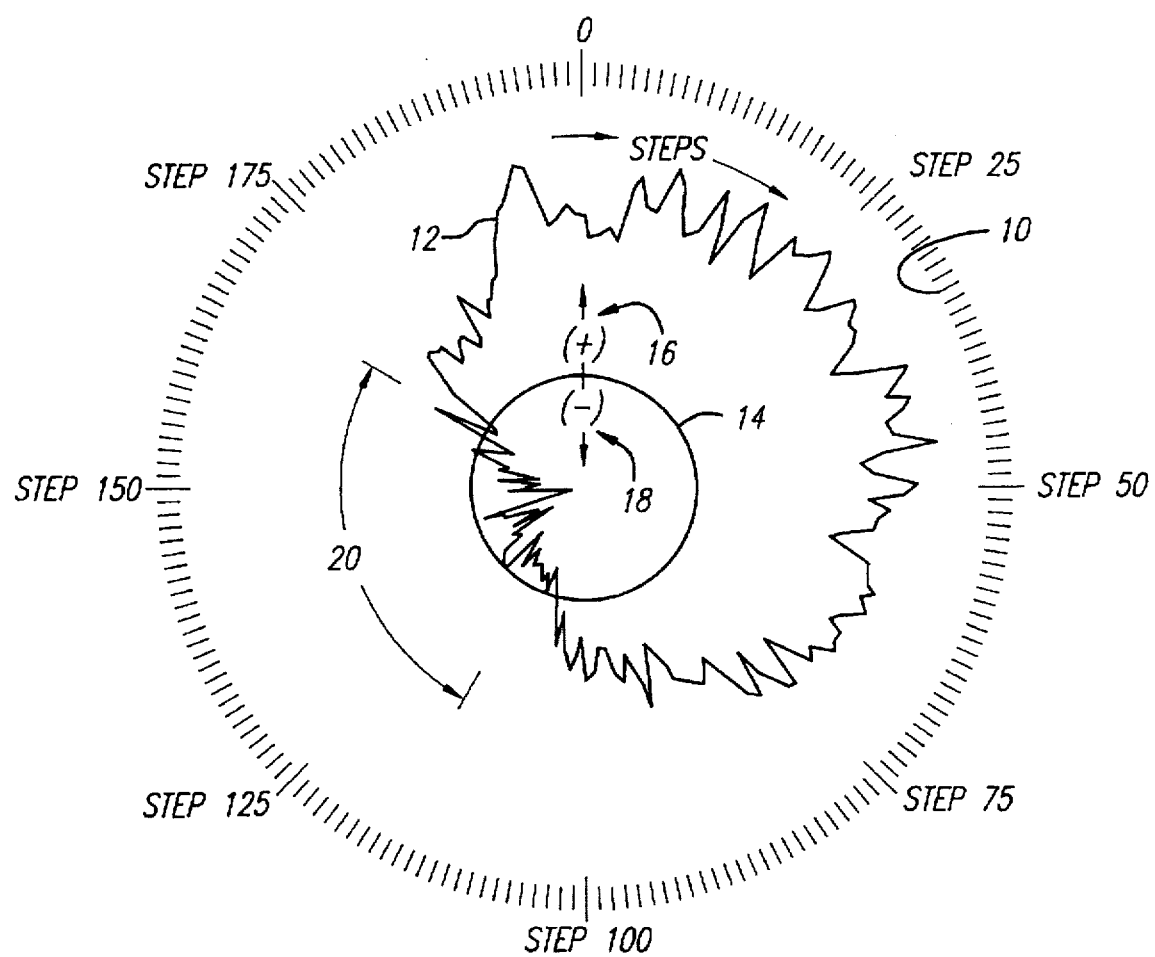
FIG. 1 is a polar graph of the volume pumped per motor step over one pump cycle of a common linear peristaltic pump.
Figure 2:
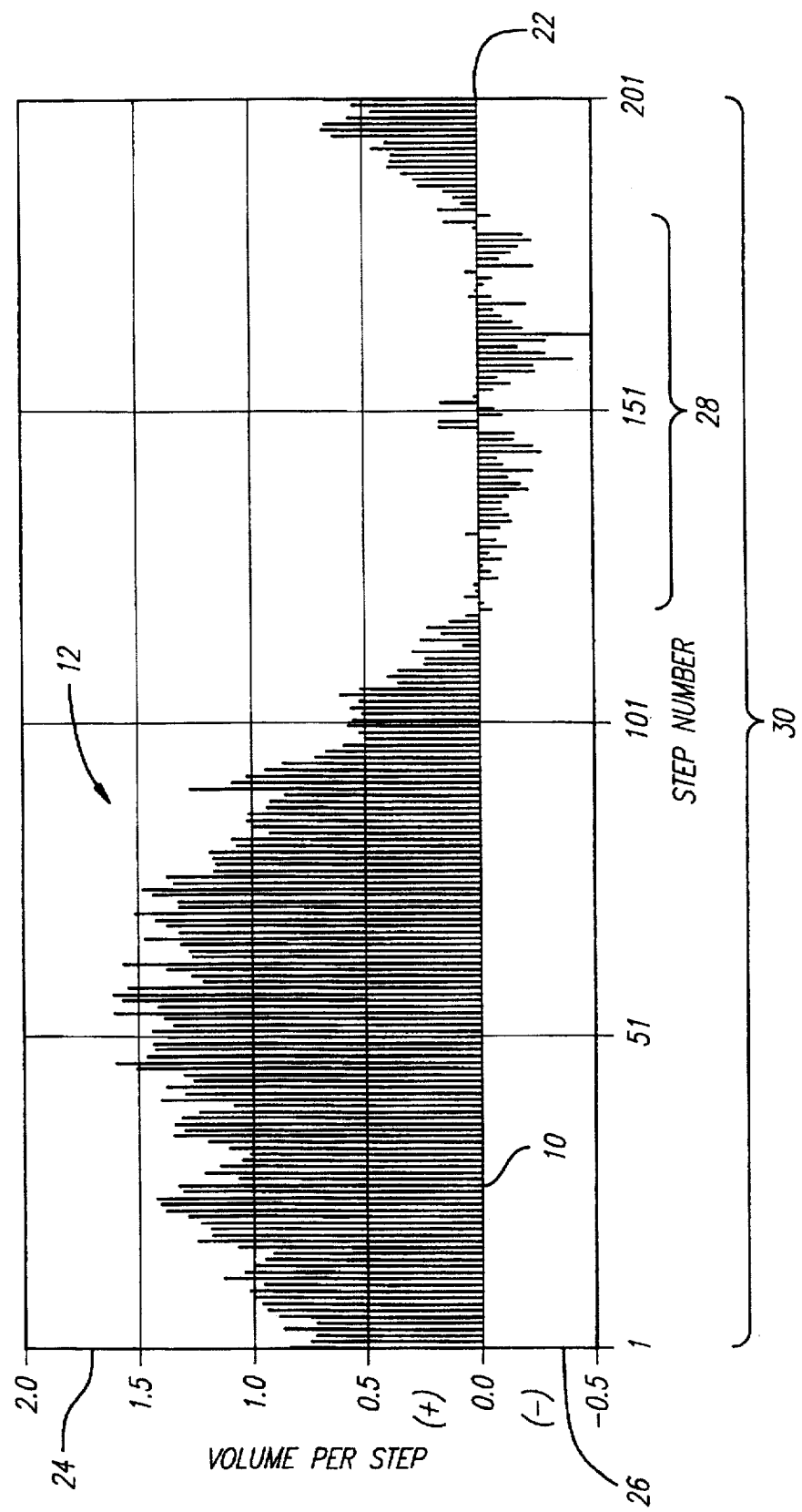
FIG. 2 is a linear graph representation of the pump cycle shown in FIG. 1.
Figure 3:
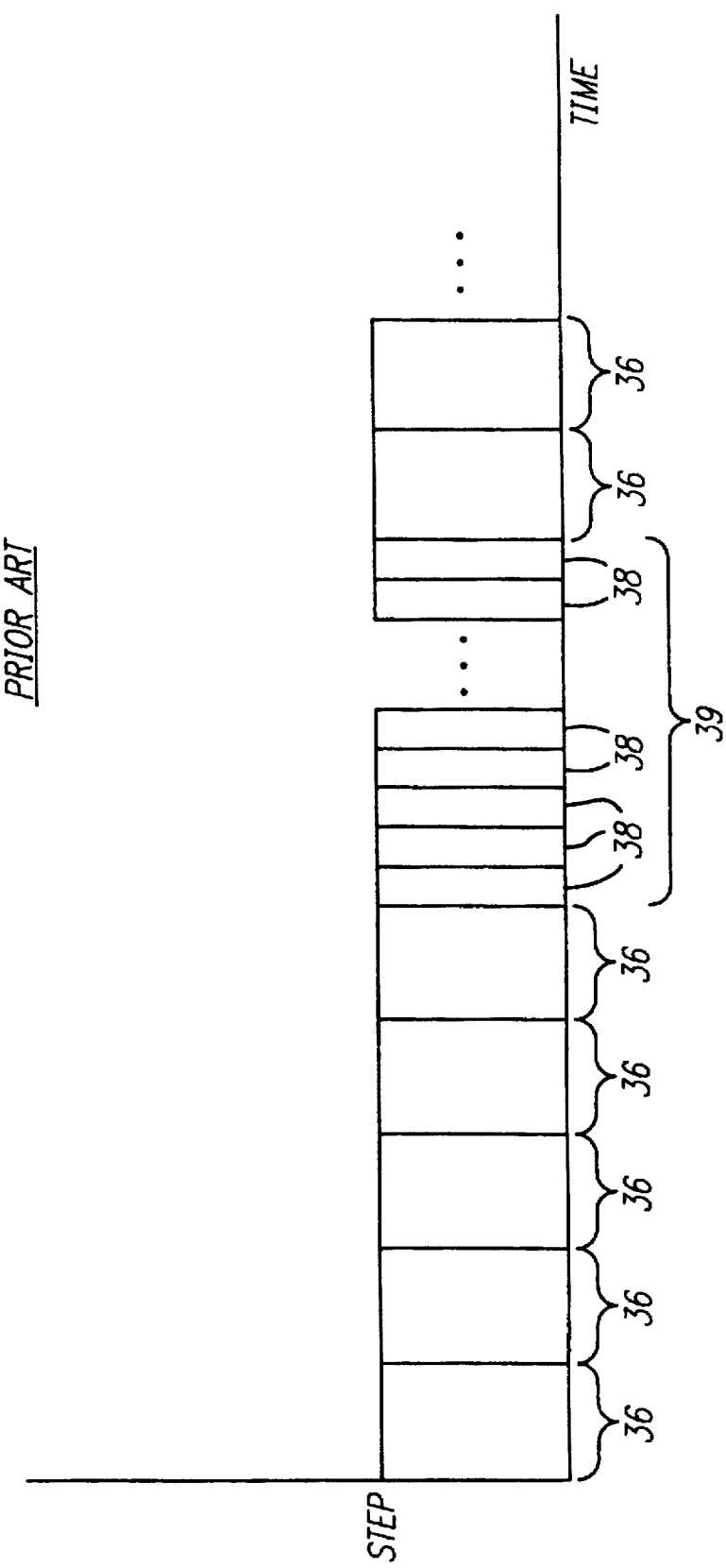
FIG. 3 is a linear graph representation of the motor steps of a step motor illustrating a speed-up cycle.

Because of the mechanical connections of the drive motor 56 with the cam shaft 54, the cam shaft with the cams 52, the cams with the pumping fingers 58, and the fingers with the tubing 44, each step moved by the cam shaft and step motor results in a certain step volume of fluid being pumped through the tubing, either in one direction or the other. As shown in FIGS. 1 and 2, the flow pattern is less than uniform even having a segment of negative flow. The amount of fluid flow corresponding to each step of the motor is stored in a memory 64 for later use as described below in detail.

The fluid delivery system 40 has a microprocessor 66 that communicates with the memory 64. The microprocessor also communicates with the position sensor 60 to determine the position of the motor and cams. The microprocessor 66 is provided with an operator input unit or key pad 68 through which an operator may set the desired flow rate and other pumping parameters. The memory 64 may contain in addition to the step volume as described above, alarm thresholds, and other preprogrammed parameters.

Figure 5:
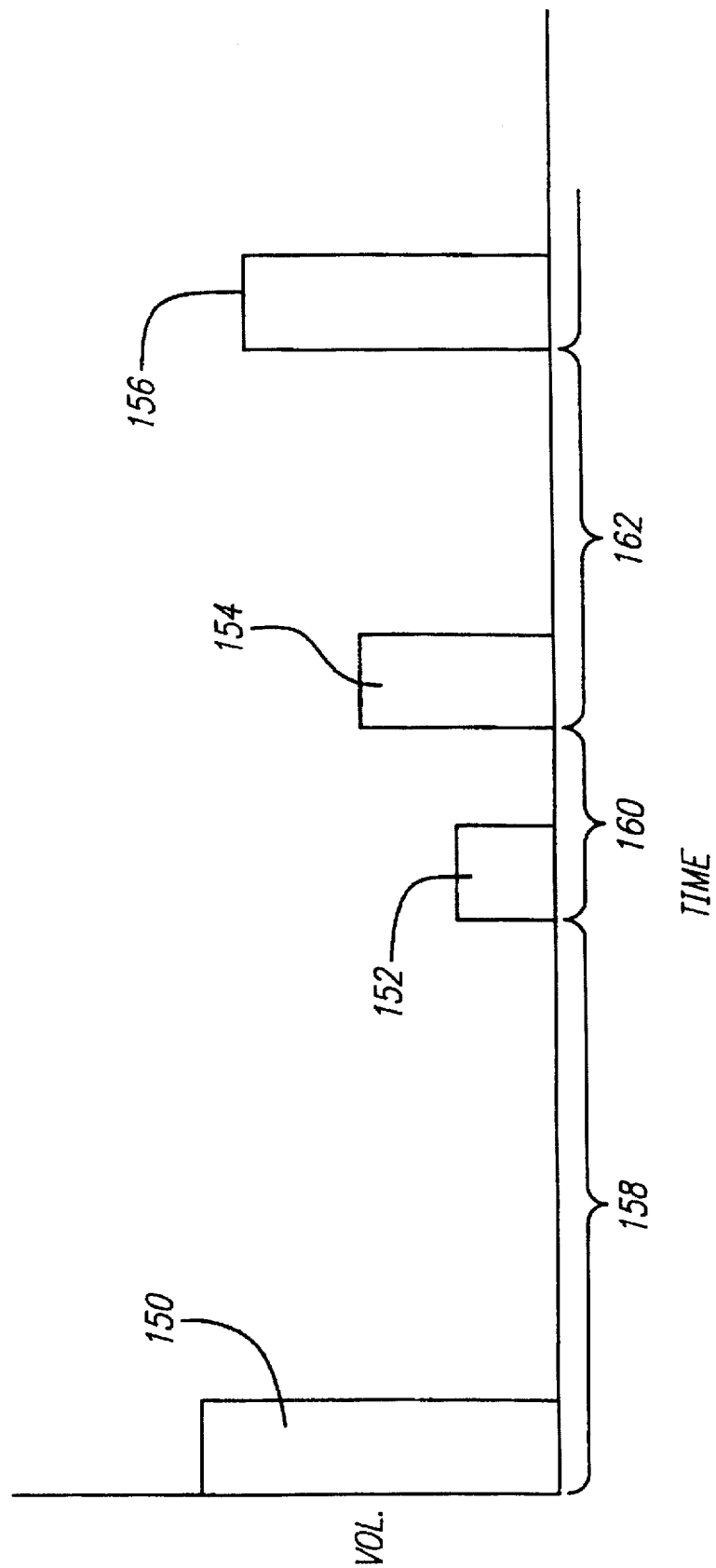
FIG. 5 is a graph illustrating different incremental volumes resulting from incremental movement of the pumping mechanism and different spacing between the incremental movements to increase flow uniformity.

Referring now to FIG. 5, a system for increasing the flow uniformity of a pumping mechanism that provides varying volume increments is shown. The first volume increment 150 is much larger than subsequent volume increments 152, 154, and 156. Thus, the spacing 158 of that volume increment to the next increment is larger than the spacing 160 between the second volume increment 152 and the increment subsequent 154 to it. Because the third increment 154 is larger than the than the second, the spacing 162 between it and the subsequent increment 156 is larger than the spacing between the spacing between the second 152 and third 154 increments. Thus, the spacing is directly proportional to the volume in the increment; the larger the volume increment, the larger the spacing. Viewing each increment from a time viewpoint, it can be seen that the flow may be made uniform because the time between volume increments can be adjusted to compensate for variances in flow. Flow uniformity will therefore be increased.

Figure 6:
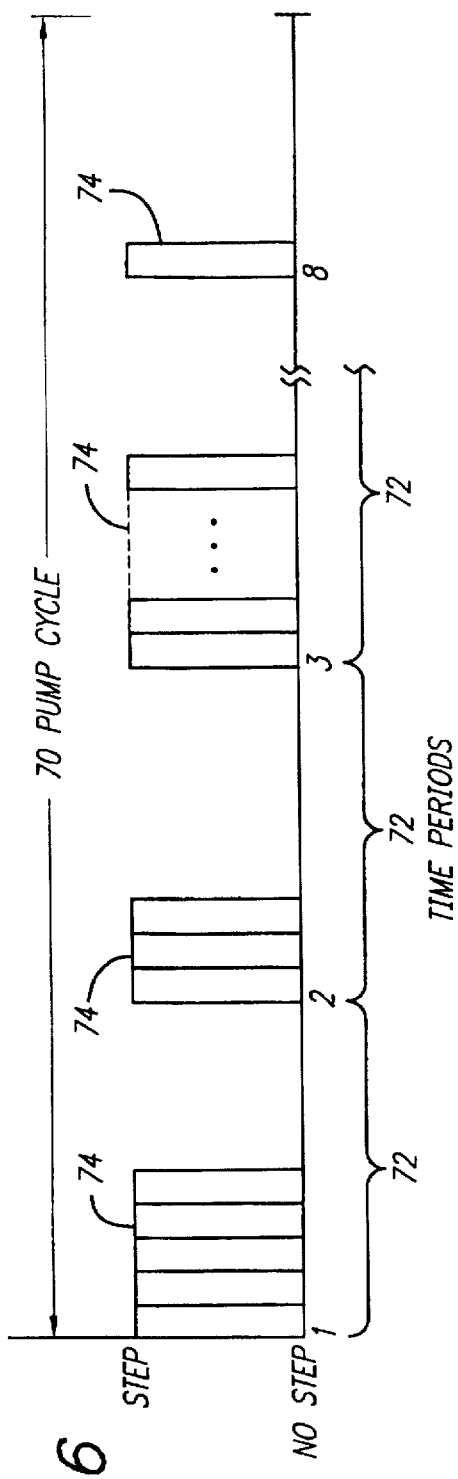
FIG. 6 is a linear graph representation illustrating the grouping of sequential motor steps in time periods in accordance with one aspect of the invention.
Figure 7:
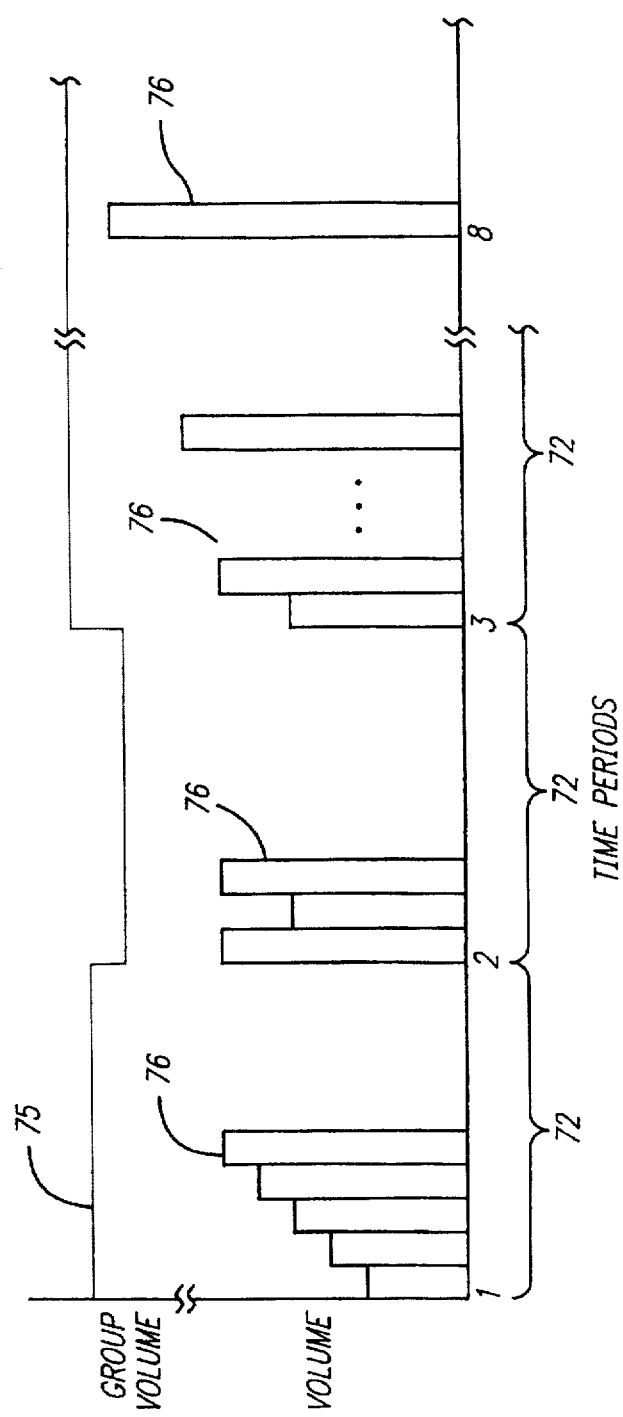
FIG. 7 is a linear graph representation of volumetric flow superimposed over the time periods shown in FIG. 6 demonstrating increased flow uniformity.

Referring now to FIGS. 6 and 7, a system for increasing flow uniformity over a pump cycle in accordance with an aspect of the invention is shown. In this aspect, groups of steps are formed to increase flow uniformity. A complete pump cycle period 70 has been divided into a plurality of equal time periods 72, in this case eight periods. These periods are labeled as "1", "2", "3", etc. Based on the volumetric flow rate selected by the pump operator, a target volume to be pumped in each time period is calculated.

The processor 66 (FIG. 4) then groups a number of sequential motor steps in each time period to result in a volume pumped that is as close to the target volume as possible. The exact number of steps assigned to each step group 74 is dependent on the particular step volume of each step that is available for the group and consequently, the summation of most step group volumes 76 in a time period will go over or under the target volume. As each sequential step is considered, the processor determines if adding that step would cause the group volume 76 to differ more from the target volume than it would if the step were not added. If adding the step would cause a greater difference, that step is not assigned to the present group but becomes the first step of the immediately subsequent group.

FIG. 6 present the grouping of a number of steps into discrete groups of steps 74. As is shown, the first group has five steps, the second group has three steps. The time frame 72 for each group of steps 74 is the same as the time frame for other groups. FIG. 7 presents the volume per step 76 and the summation of the step volumes to equal a group volume 75. As is shown, the group volumes vary slightly.

Turning now to FIG. 8, a table of groups of steps is presented. The heading of the table presents target volumes 77 to be pumped by each group of steps. The target volume increases as the flow rate selected increases. As shown, there are four columns of target volumes ranging from five micro-liters to forty micro-liters. The next row 79 shows the number of groups of steps in a pump cycle. The number varies in dependence on the target volume. At the lowest target volume, there are thirty-two groups of steps. At the largest target volume there are only four groups of steps. Although not shown, other target volumes may be selected and other numbers of groups of steps.

The remainder of each column presents the numbers of subsequent steps in each group. For example, in the column of the five micro-liters target volume, the first group has three steps in it. The second group has four steps. The third to last group of steps contains ninety-four steps, this including the negative flow region. Referring briefly to the column for the target volume of forty micro-liters, the first group of steps has twenty-five steps while the last group has one hundred and twenty-seven steps.

The processor 66 (FIG. 4) selects the number of time periods 79 or step groups per pumping cycle based on the flow rate selected with the number of time periods selected being inversely proportional to a flow rate selected 77. Also, the larger the target volume, the larger the number of steps in a group of steps.

Figure 9:
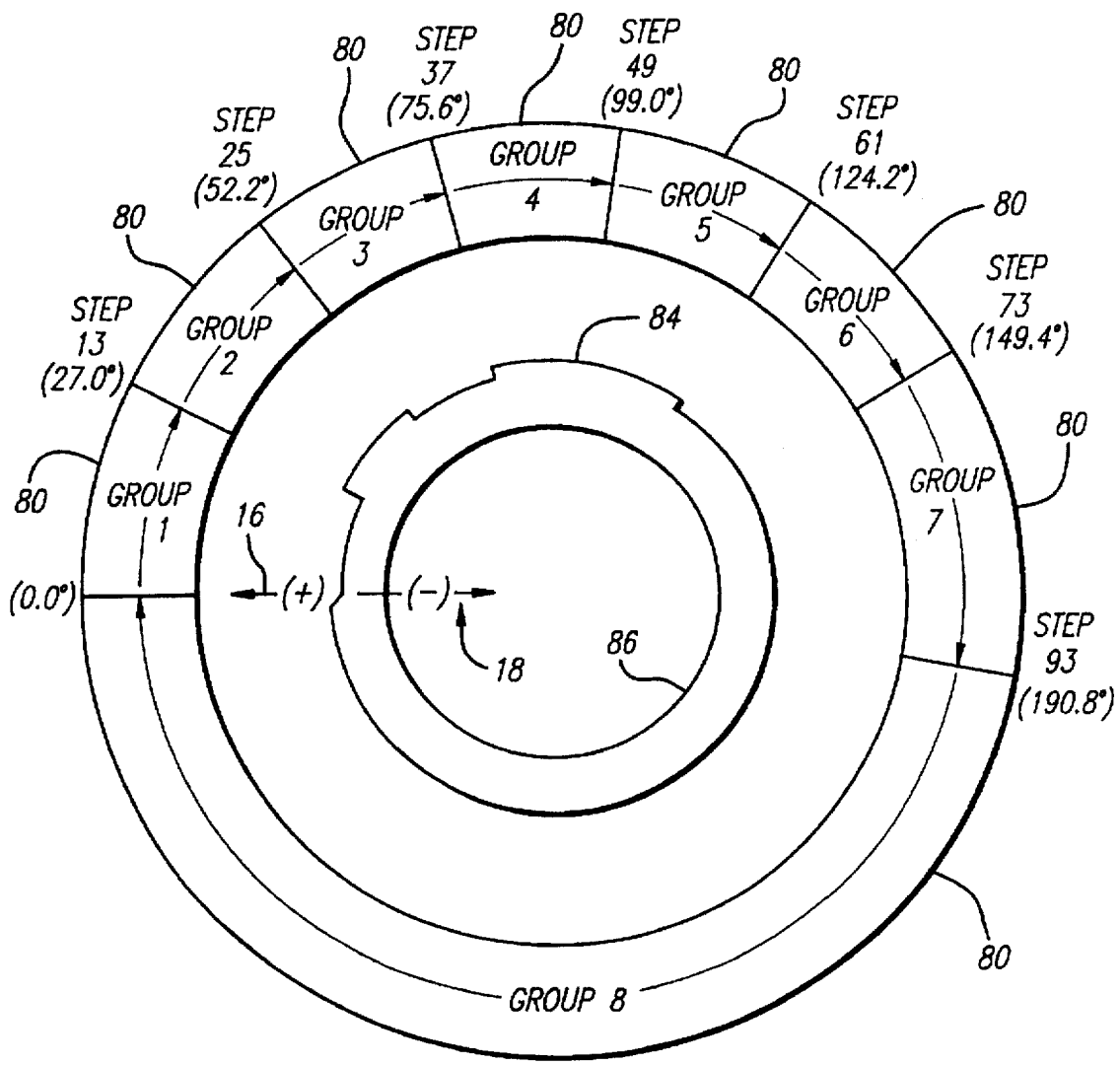
FIG. 9 is a polar graph representation of the groupings of sequential steps of a motor in accordance with an aspect of the invention and shows the increased flow uniformity over the pump cycle resulting from the groupings.

FIGS. 9 and 10, graphically illustrate the more uniform flow rate over a pumping cycle as a result of one embodiment of the invention. In this case, there were eight groups of steps 80 over a complete motor rotation or pump cycle 82 of two-hundred steps. In each step group 80, the motor steps are moved as shown in the example of FIG. 6. The resulting flow pattern 84 is much more uniform than those patterns shown in FIGS. 1 and 2. The reference circle/line 86 establishes a zero flow reference. Flow plotted outside/above the line is positive flow and flow plotted inside/below the line is negative flow. When pumping in groups in accordance with the invention rather than continuously in incremental pump steps, the flow uniformity increases. The angles given in FIG. 9 and the marks along the horizontal axis 86 in FIG. 10 are approximations and are included for illustration only.

The motor steps shown in FIGS. 6 and 7 have been exaggerated for clarity in illustration. There may be much more time left between the last step in one group and the first step in the next group than that shown in the figures. Depending on the flow rate selected, the number groups of steps, and the number of steps in a group, the step motor may achieve the number of steps assigned to a particular step group in a small fraction of the step group time frame. After moving the assigned number of steps, the motor does not rotate farther, until the beginning of the next group of steps. During this "dead time," the pressure sensor may monitor the pressure response waveform in the fluid line and/or other tasks may be accomplished.

This approach of grouping of steps also conserves electrical energy because the motor is not always moving. Additionally, when it is moving, typically more than one step is moved continuously. Thus, the extra power needed for starting the step motor occurs less frequently. Such energy conservation becomes important where the pump is operated by battery power.

Different means are known for determining the volume pumped per motor step. These means include, for example, gravimetric mass measurement and pressure wave integration using the IRMA method as disclosed in U.S. Pat. No. 5,5,087,245 to Doan which determines flow rate by measuring flow resistance at the pump outlet. The system memory 64 may thereafter store each step volume for later use by the processor 66 in establishing step groups 74 (FIG. 5). In an alternative approach, the particular groups of steps and the group volumes may be stored in memory 64 for each flow rate or target volume and later retrieved by the processor 66 once the flow rate has been selected by the operator.

Figure 11A:
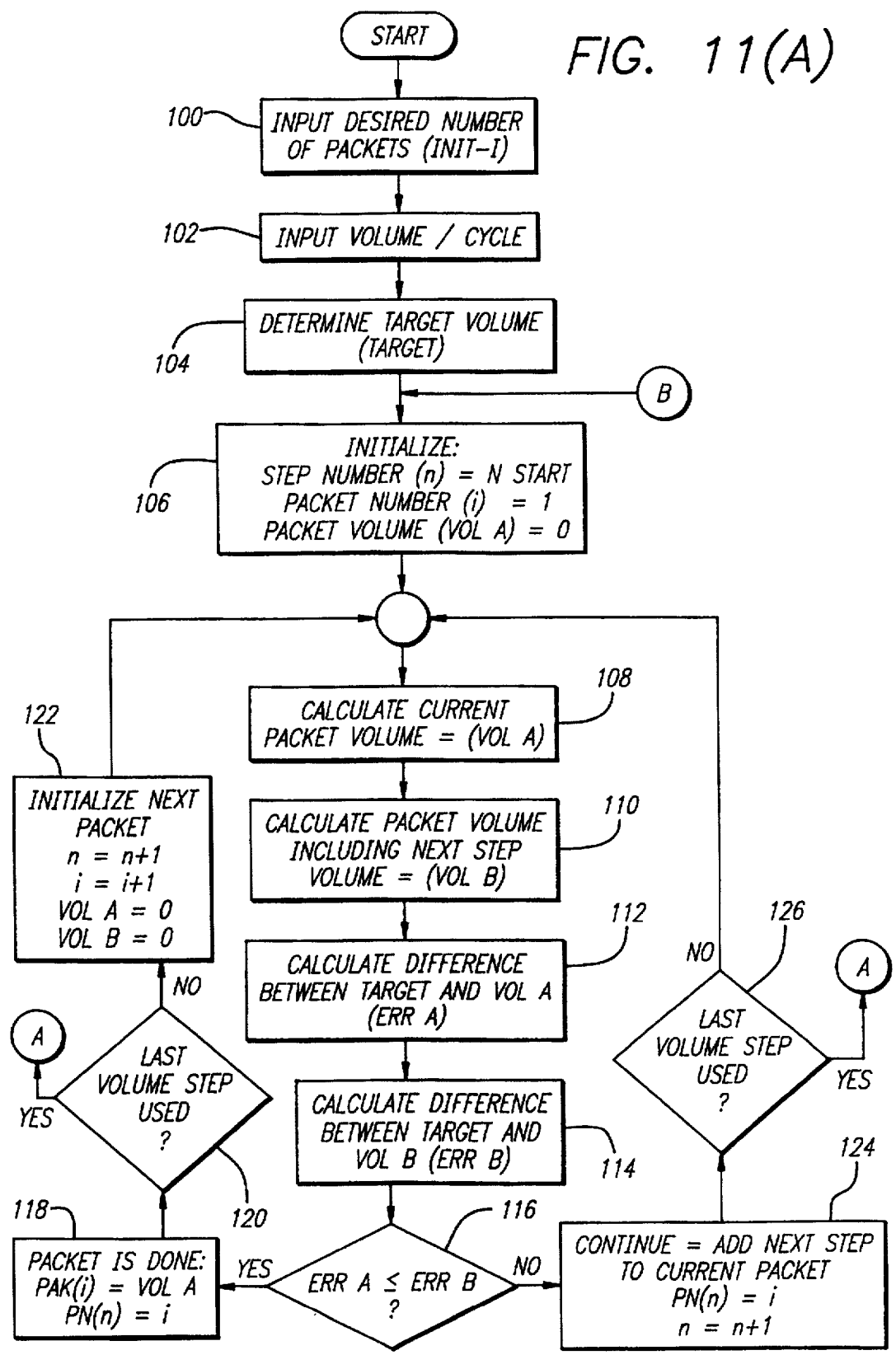
FIG. 11 illustrates a flow chart of a process of grouping sequential steps of a pumping mechanism in accordance with aspects of the invention for increasing flow uniformity.
Figure 11B:
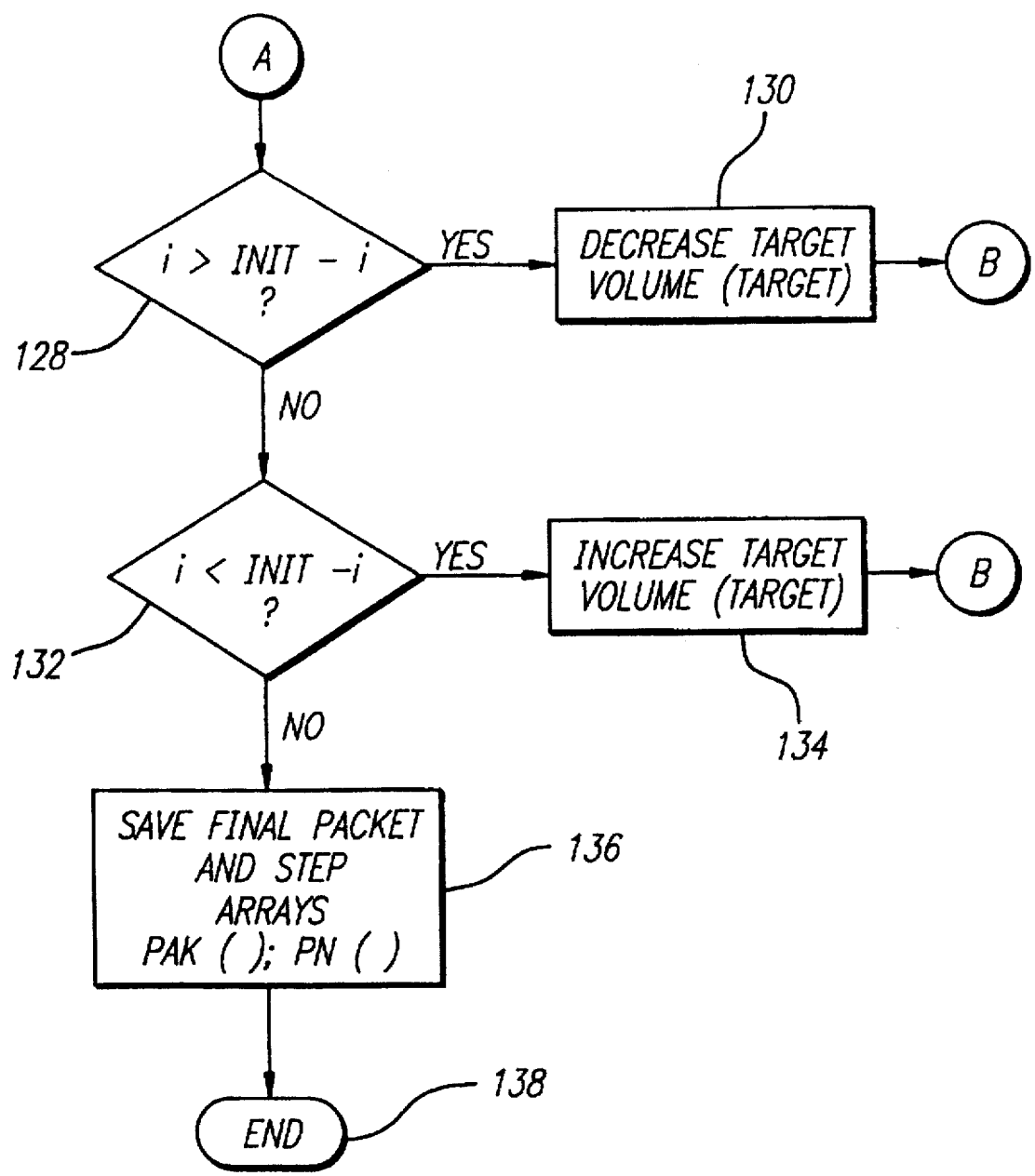

Referring now to FIG. 11, a flow chart directed to the process of assigning steps to groups of steps is shown. The process shown divides the pump cycle into time periods and organizes sequential pump step volumes into group volumes per time period for more uniform volumetric flow over the pump cycle. To provide a more uniform pump cycle flow rate, the operator at the start of the routine inputs the number of equal time periods (groups) per cycle INIT-I 100 and then selects a pump cycle flow rate corresponding to a volume per pump cycle 102. A target volume, TARGET, per time period is then calculated 104 by dividing the selected volume per pump cycle by the number of selected time periods.

The step number in the cycle NSTART is set in memory; the step group number i is initialized to one for the first period, and the group volume VolA is initialized to zero 106. The volume of the current step group is calculated 108. If this is the beginning of a pump cycle, that volume will consist of the volume of the first step. This calculated volume is denoted VolA. The volume of the next sequential step is added to VolA to result in VolB 110. Next, the differences between VolA and the target volume (ErrA) and VolB and the target volume (ErrB) are calculated 112 and 114 respectively. These differences are then compared to each other 116. If ErrA is less than or equal to ErrB, that step group is considered complete and no more steps, including the step just considered, will be added to the group 118. The VolA is then assigned as the group volume PAK (i) and the group number is also assigned PN (n).

The motor position is then evaluated to determine if the pumping cycle is complete 120. If the pumping cycle is not complete and more pump steps remain in the cycle, the group volume and number are initialized 122 and the process of calculating the volumes and the differences 108–116 is repeated for this new step group.

In the event that ErrA was greater than ErrB, that step will be added to the step group 124 and a determination will then be made as to whether this is the last step in the pumping cycle 126. If this is not the last step, the process of calculating VolA, VolB and the above-discussed differences and comparisons 108–116 will be conducted.

When all steps of the cycle have been used, the process moves to process step "A" to compare the number of group volumes i generated with the number of time periods input by the operator. If the number of group volumes developed is greater than the number of time periods selected 128, the target volume TARGET is decreased and the process is begun again at "B" If the number of group volumes developed is less than the number of time periods selected 132, the target volume, TARGET is increased 134 and the process is begun again at "B". If the number of group volumes developed is equal to the selected number of time periods 136, the final step groups are saved 136 in memory and the process ends 138. The processor may then retrieve the step groups as needed during its control of the motor.

To inform the processor of the position of the pumping mechanism so that the particular step volumes can be determined, a position location system coupled to the cam shaft or other moving part of the pumping mechanism may be used. One technique for locating the position of the peristaltic mechanism in its cycle is the use of an optical disk mounted to rotate with the mechanism and having markings indicative of the location of the mechanism in that cycle. Such a system is shown and described in the patent application entitled "SYSTEM FOR DETERMINING PUMPING POSITION WHILE LIMITING VOLUME OF FLUID PUMPED" by Charles R. Holdaway and Eric A. Warner having Ser. No. 08/304,582, now Pat. No. 5,534,692, incorporated herein by reference.

Although a step motor has been described above, this is for illustration purposes only. Other motors providing incremental movement may be also be used.

It will be apparent from the foregoing that while particular forms of the invention have been illustrated and described, various modification can be made without departing from the spirit and scope of the invention. Accordingly, it is not intended that the invention be limited, except as by the appended claims.

What is claimed is:

1. A system for increasing the uniformity of flow of fluid through a conduit comprising:

a drive device that moves in movement increments;

a pumping mechanism coupled to the drive device that pumps fluid through the conduit in volume increments in response to movement increments of the drive device, each volume increment corresponding to a respective movement increment of the drive device, at least some of the volume increments differing from other volume increments; and a processor configured to control the drive device to space the movement increments by an amount of time directly proportional to the volume increments corresponding to the respective movement increments.

2. The system according to claim 1 wherein:

the drive device comprises a step motor coupled to the pumping mechanism, each step of the step motor resulting in a respective volume increment;

the processor is configured to control the step motor to space the steps by an amount directly proportional to the volume increments corresponding to the respective steps.

3. The system according to claim 2 wherein the pumping mechanism comprises a linear peristaltic mechanism having a plurality of peristaltic fingers, one of which is a downstream finger, all of which are movable into and out of engagement with the conduit, the movement of the fingers being controlled by the step motor.

4. The system according to claim 3 wherein the processor is configured to control the step motor to continuously move through a predetermined number of step motor to delay in the event that negative flow would result with a movement of a peristaltic finger.

5. The system according to claim 1 wherein:

the processor is configured to control the drive device to move continuously through predetermined numbers of movement increments to form a plurality of groups of movement increments; and the processor is configured to control the drive device to space movement between groups of movement increments by an amount of time directly proportional to the sum of the volume increments corresponding to the respective group of movement increments.

6. The system according to claim 5 wherein:

the processor is configured to select the number of movement increments included in each group of movement increments to result in the sums of the volume increments of each group of movement increments being approximately equal.

7. The system according to claim 5 in which the processor is configured to be responsive to a selected flow rate and wherein the processor is configured to vary the number of movement increments in each group of movement increments in dependence upon the selected flow rate.

8. The system according to claim 7 wherein the processor is configured to decrease the number of groups of movement increments and increase the number of movement increments in each group as the flow rate increases.

9. A system for controlling the flow of fluid through a conduit in response to a selected flow rate to provide more uniform flow, the system comprising:

a pumping mechanism acting on the conduit to move fluid through the conduit, the mechanism acting in movement increments wherein each movement increment causes a respective volume increment of fluid to flow in the conduit;

a processor configured to control the pumping mechanism to move through a number of movement increments to from groups of movement increments with the sum of the volume increments of each group of movement increments being approximately the same as the sum of volume increments of the other groups of movement increments.

10. The system of claim 9 wherein the processor is configured to control the pumping mechanism to move continuously through the movement increments in each group of movement increments.

11. The system of claim 9 wherein:

the processor is configured to control the pumping mechanism to move through each group of movement increments within a predetermined time period; and the processor is configured to control the pumping mechanism to continuously move through the movement increments in each group during one portion of the time period and to not move during the remaining portion of the time period.

12. The system of claim 11 wherein the processor is configured to control the pumping mechanism to continuously move through the movement increments of each group of movement increments at the beginning of the respective time period and the to not move for the remainder of the respective time period.

13. The system of claim 9 wherein:

the pumping mechanism comprises a linear peristaltic mechanism having a plurality of peristaltic fingers having a downstream finger, the fingers movable into and out of engagement with the conduit to control the flow of fluid through the conduit; and the processor is configured to control the pumping mechanism to continuously move through a predetermined number of movement increments without delay during the disengagement of the downstream finger from the fluid conduit.

14. The system of claim 9 wherein the processor is configured to select the number of groups based on the flow rate selected with the number of groups being inversely proportional to the flow rate and the volume of each group being directly proportional to the flow rate.

15. A method for providing more uniform flow of fluid through a conduit acted on by a pumping mechanism, the pumping mechanism moving in movement increments with each movement increment causing a particular volume increment of fluid flow through the conduit, the pumping mechanism having a pumping cycle and being responsive to a selected flow rate, the method comprising:

controlling the pumping mechanism to space the movement increments by an amount of time directly proportional to the volume increments corresponding to the respective movement increments.

16. The method of claim 15, comprising the further step of:

retrieving data representing the volume increments corresponding to the respective movement increments.

17. The method of claim 16, comprising the further step of:

controlling the pumping mechanism to continuously move through a predetermined number of incremental movements without delay in the event that a negative volume increment would result from a particular incremental movement.

18. The method of claim 15, wherein the pumping mechanism is a linear peristaltic mechanism having a plurality of peristaltic fingers having a downstream finger, the fingers movable into and out of engagement with the conduit to control the flow of fluid through the conduit, the method comprising the further step of:

controlling the pumping mechanism to continuously move through a predetermined number of movement increments without delay during the disengagement of the downstream finger from the fluid conduit.

19. A method for providing more uniform flow of fluid through a conduit acted on by a pumping mechanism, the pumping mechanism moving in movement increments with each movement increment causing a particular volume increment of fluid flow through the conduit, the pumping mechanism having a pumping cycle and being responsive to a selected flow rate, the method comprising:

controlling the pumping mechanism to space the movement increments by an amount of time directly proportional to the volume increments corresponding to the respective movement increments;

controlling the pumping mechanism to move continuously through predetermined numbers of movement increments to form a plurality of groups of movement increments; and controlling the pumping mechanism to space movement between groups of movement increments by an amount of time directly proportional to the sum of the volume increments corresponding to the respective group of movement increments.

20. The method according to claim 9 wherein:

forming groups of movement increments comprises selecting the number of movement increments to be included in each group of movement increments to result in the sums of the volume increments of each group of movement increments being approximately equal.

21. The method according to claim 19 wherein:

forming groups of movement increments comprises selecting the number of movement increments in each group of movement increments to increase as the selected flow rate is increased.

22. The method according to claim 21 wherein:

moving through the groups of movement increments comprises moving within a predetermined time period; and moving the movement increments in each group continuously during one portion of the time period and not moving during the remaining portion of the time period.

23. The method of claim 16 wherein moving through the movement increments in a group comprises moving continuously through the increments at the beginning of the respective time period and not moving for the remainder of the respective time period.

24. A parenteral fluid delivery system comprising:

a fluid delivery conduit;

a linear peristaltic pump, said pump having a plurality of peristaltic elements movable into and out of engagement with the conduit to control the flow of fluid through the conduit;

a drive device having a plurality of positions through which the drive device may move in incremental movements, said drive device coupled to the peristaltic elements of the pump, wherein the peristaltic elements pump fluid through the conduit in volume increments in response to incremental movements of the drive device, each volume increment corresponding to a respective incremental movement;

a position sensor that monitors the position of the drive device;

a memory that is configured to store data representing the volume increment of fluid flow corresponding to each incremental movement of the motor;

a processor in communication with the memory that is configured to receive the drive device position signal and the fluid flow volume data, process the drive device position signal with the fluid flow volume data, and, for volume increments that are positive, control the drive device to vary the timing of the incremental movements of the drive device proportionally to the volume increments corresponding to the respective incremental movements.

25. The fluid delivery system of claim 24, wherein the processor is configured to move through a predetermined number of increments without delay in the event that a volume increment for a respective incremental movement is negative.

26. The fluid delivery system of claim 24, wherein the drive device comprises a cam shaft rotated by a step motor.

* * * * *

UNITED STATES PATENT AND TRADEMARK OFFICE
CERTIFICATE OF CORRECTION

PATENT NO. : 5,716,194
DATED : Feb. 10, 1998
INVENTOR(S) : Robert D. Butterfield, Gregory I. Voss It is certified that error appears in the above-identified patent and that said Letters Patent is hereby corrected as shown below:

Column 11, Claim 20, Line 11, change "9", to read --19--.

Signed and Sealed this

Sixteenth Day of June, 1998

Attest:

BRUCE LEHMAN

Attesting Officer          Commissioner of Patents and Trademarks